United States Patent
Dresher (10) Patent No.: US 9,770,293 B2
(45) Date of Patent: Sep. 26, 2017

(54) SYSTEMS AND METHODS FOR TREATING TISSUE OF A PASSAGEWAY WITHIN A BODY

(71) Applicant: Boston Scientific Scimed, Inc., Maple Grove, MN (US)

(72) Inventor: Russell P. Dresher, Hudson, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1169 days.

(21) Appl. No.: 13/895,771

(22) Filed: May 16, 2013

(65) Prior Publication Data

US 2013/0324995 A1 Dec. 5, 2013

Related U.S. Application Data

(60) Provisional application No. 61/655,229, filed on Jun. 4, 2012.

(51) Int. Cl.
*A61B 18/12* (2006.01)
*A61B 18/18* (2006.01)
(Continued)

(52) U.S. Cl.
CPC .......... *A61B 18/18* (2013.01); *A61B 18/1485* (2013.01); *A61B 18/1492* (2013.01);
(Continued)

(58) Field of Classification Search
CPC ................ A61B 18/1492; A61B 18/18; A61B 2018/0016; A61B 2018/00214;
(Continued)

(56) References Cited

U.S. PATENT DOCUMENTS

| 612,724 A | 10/1898 | Hamilton |
| 1,155,169 A | 9/1915 | Starkweather |

(Continued)

FOREIGN PATENT DOCUMENTS

| DE | 19529634 A1 | 2/1997 |
| EP | 189329 A3 | 6/1987 |

(Continued)

OTHER PUBLICATIONS

Jarrard et al., A theoretical model of the application of RF energy to the airway wall and its experimental validation, BioMedical Engineering Online 2010, 9:81, pp. 1-17.
(Continued)

*Primary Examiner* — Thomas Giuliani
(74) *Attorney, Agent, or Firm* — Bookoff McAndrews, PLLC (57) ABSTRACT

The present disclosure is directed to a method for treating tissue in a passageway within a body. The method may include positioning a medical device adjacent a treatment site in the passageway. The medical device may include an elongate member having a proximal end and a distal end, and an energy emitting portion positioned adjacent the distal end. The method may further include supplying an amount of energy from an energy source to the energy emitting portion. A first portion of the amount of the energy may be transmitted through the energy emitting portion to the tissue and a second portion of the amount of energy may be reflected from the energy emitting portion. The method may further include monitoring a signal corresponding to one of the first portion of the amount of energy and the second portion of the amount of energy.

18 Claims, 5 Drawing Sheets

(51) Int. Cl.
*A61B 18/14* (2006.01)
*A61B 18/00* (2006.01)
*A61B 90/00* (2016.01)

(52) U.S. Cl.
CPC .............. *A61B 2018/0016* (2013.01); *A61B 2018/00214* (2013.01); *A61B 2018/00267* (2013.01); *A61B 2018/00541* (2013.01); *A61B 2018/00636* (2013.01); *A61B 2018/00642* (2013.01); *A61B 2018/00666* (2013.01); *A61B 2018/00672* (2013.01); *A61B 2018/00678* (2013.01); *A61B 2018/00708* (2013.01); *A61B 2018/00779* (2013.01); *A61B 2018/00785* (2013.01); *A61B 2018/00875* (2013.01); *A61B 2090/065* (2016.02)

(58) Field of Classification Search
CPC .. A61B 2018/1861; A61B 2018/00642; A61B 2018/00666; A61B 2018/00708; A61B 2018/00785; A61B 2018/00541; A61B 2018/00636; A61B 2018/00779; A61B 2018/00875; A61B 2018/0022; A61B 2018/00267
USPC ........................................ 606/33, 34, 38, 42
See application file for complete search history.

(56) References Cited

U.S. PATENT DOCUMENTS

| | | |
|---|---|---|
| 1,207,479 A | 12/1916 | Bisgaard |
| 1,216,183 A | 2/1917 | Swingle |
| 2,072,346 A | 3/1937 | Smith |
| 3,320,957 A | 5/1967 | Sokolik |
| 3,568,659 A | 3/1971 | Karnegis |
| 3,667,476 A | 6/1972 | Muller |
| 3,692,029 A | 9/1972 | Adair |
| 3,995,617 A | 12/1976 | Watkins et al. |
| 4,095,602 A | 6/1978 | Leveen |
| 4,116,589 A | 9/1978 | Rishton |
| 4,129,129 A | 12/1978 | Amrine |
| 4,154,246 A | 5/1979 | LeVeen |
| 4,461,283 A | 7/1984 | Doi |
| 4,502,490 A | 3/1985 | Evans et al. |
| 4,503,855 A | 3/1985 | Maslanka |
| 4,512,762 A | 4/1985 | Spears |
| 4,522,212 A | 6/1985 | Gelinas et al. |
| 4,557,272 A | 12/1985 | Carr |
| 4,565,200 A | 1/1986 | Cosman |
| 4,567,882 A | 2/1986 | Heller |
| 4,584,998 A | 4/1986 | McGrail |
| 4,612,934 A | 9/1986 | Borkan |
| 4,621,642 A | 11/1986 | Chen |
| 4,621,882 A | 11/1986 | Krumme |
| 4,625,712 A | 12/1986 | Wampler |
| 4,643,186 A | 2/1987 | Rosen et al. |
| 4,646,737 A | 3/1987 | Hussein et al. |
| 4,674,497 A | 6/1987 | Ogasawara |
| 4,683,890 A | 8/1987 | Hewson |
| 4,704,121 A | 11/1987 | Moise |
| 4,706,688 A | 11/1987 | Don Michael et al. |
| 4,709,698 A | 12/1987 | Johnston et al. |
| 4,739,759 A | 4/1988 | Rexroth et al. |
| 4,754,065 A | 6/1988 | Levenson et al. |
| 4,754,752 A | 7/1988 | Ginsburg et al. |
| 4,765,959 A | 8/1988 | Fukasawa |
| 4,772,112 A | 9/1988 | Zider et al. |
| 4,773,899 A | 9/1988 | Spears |
| 4,779,614 A | 10/1988 | Moise |
| 4,784,135 A | 11/1988 | Blum et al. |
| 4,790,305 A | 12/1988 | Zoltan et al. |
| 4,799,479 A | 1/1989 | Spears |
| 4,802,492 A | 2/1989 | Grunstein |
| 4,817,586 A | 4/1989 | Wampler |
| 4,825,871 A | 5/1989 | Cansell |
| 4,827,935 A | 5/1989 | Geddes et al. |
| 4,846,152 A | 7/1989 | Wampler et al. |
| 4,862,886 A | 9/1989 | Clarke et al. |
| 4,895,557 A | 1/1990 | Moise et al. |
| 4,906,229 A | 3/1990 | Wampler |
| 4,907,589 A | 3/1990 | Cosman |
| 4,908,012 A | 3/1990 | Moise et al. |
| 4,920,978 A | 5/1990 | Colvin |
| 4,944,722 A | 7/1990 | Carriker et al. |
| 4,955,377 A | 9/1990 | Lennox et al. |
| 4,967,765 A | 11/1990 | Turner et al. |
| 4,969,865 A | 11/1990 | Hwang et al. |
| 4,976,709 A | 12/1990 | Sand |
| 4,985,014 A | 1/1991 | Orejola |
| 4,991,603 A | 2/1991 | Cohen et al. |
| 5,009,636 A | 4/1991 | Wortley et al. |
| 5,009,936 A | 4/1991 | Yamanaka et al. |
| 5,010,892 A | 4/1991 | Colvin et al. |
| 5,019,075 A | 5/1991 | Spears et al. |
| 5,027,829 A | 7/1991 | Larsen |
| 5,030,645 A | 7/1991 | Kollonitsch |
| 5,036,848 A | 8/1991 | Hewson |
| 5,053,033 A | 10/1991 | Clarke |
| 5,056,519 A | 10/1991 | Vince |
| 5,074,860 A | 12/1991 | Gregory et al. |
| 5,078,716 A | 1/1992 | Doll |
| 5,084,044 A | 1/1992 | Quint |
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,105,826 A | 4/1992 | Smits et al. |
| 5,106,360 A | 4/1992 | Ishiwara et al. |
| 5,107,830 A | 4/1992 | Younes |
| 5,114,423 A | 5/1992 | Kasprzyk et al. |
| 5,116,864 A | 5/1992 | March et al. |
| 5,117,828 A | 6/1992 | Metzger et al. |
| 5,135,517 A | 8/1992 | McCoy |
| 5,152,286 A | 10/1992 | Sitko et al. |
| 5,165,420 A | 11/1992 | Strickland |
| 5,167,223 A | 12/1992 | Koros et al. |
| 5,170,803 A | 12/1992 | Hewson et al. |
| 5,174,288 A | 12/1992 | Bardy et al. |
| 5,188,602 A | 2/1993 | Nichols |
| 5,191,883 A | 3/1993 | Lennox et al. |
| 5,213,576 A | 5/1993 | Abiuso et al. |
| 5,215,103 A | 6/1993 | Desai |
| 5,231,996 A | 8/1993 | Bardy et al. |
| 5,232,444 A | 8/1993 | Just et al. |
| 5,234,456 A | 8/1993 | Silvestrini |
| 5,254,088 A | 10/1993 | Lundquist et al. |
| 5,255,678 A | 10/1993 | Deslauriers et al. |
| 5,255,679 A | 10/1993 | Imran |
| 5,265,604 A | 11/1993 | Vince |
| 5,269,758 A | 12/1993 | Taheri |
| 5,281,218 A | 1/1994 | Imran |
| 5,292,331 A | 3/1994 | Boneau |
| 5,293,869 A | 3/1994 | Edwards et al. |
| 5,309,910 A | 5/1994 | Edwards et al. |
| 5,313,943 A | 5/1994 | Houser et al. |
| 5,324,284 A | 6/1994 | Imran |
| 5,334,193 A | 8/1994 | Nardella |
| 5,343,936 A | 9/1994 | Beatenbough et al. |
| 5,345,936 A | 9/1994 | Pomeranz et al. |
| 5,366,443 A | 11/1994 | Eggers et al. |
| 5,368,591 A | 11/1994 | Lennox et al. |
| 5,370,644 A | 12/1994 | Langberg |
| 5,370,679 A | 12/1994 | Atlee, III |
| 5,374,287 A | 12/1994 | Rubin |
| 5,383,917 A | 1/1995 | Desai et al. |
| 5,393,207 A | 2/1995 | Maher et al. |
| 5,394,880 A | 3/1995 | Atlee, III |
| 5,396,887 A | 3/1995 | Imran |
| 5,400,778 A | 3/1995 | Jonson et al. |
| 5,400,783 A | 3/1995 | Pomeranz et al. |
| 5,411,025 A | 5/1995 | Webster |
| 5,415,166 A | 5/1995 | Imran |
| 5,415,656 A | 5/1995 | Tihon et al. |

(56) References Cited

U.S. PATENT DOCUMENTS

| | | |
|---|---|---|
| 5,417,687 A | 5/1995 | Nardella et al. |
| 5,422,362 A | 6/1995 | Vincent et al. |
| 5,423,744 A | 6/1995 | Gencheff et al. |
| 5,423,811 A | 6/1995 | Imran et al. |
| 5,425,023 A | 6/1995 | Haraguchi et al. |
| 5,425,703 A | 6/1995 | Feiring |
| 5,425,811 A | 6/1995 | Mashita |
| 5,431,696 A | 7/1995 | Atlee, III |
| 5,433,730 A | 7/1995 | Alt |
| 5,437,665 A | 8/1995 | Munro |
| 5,443,470 A | 8/1995 | Stern et al. |
| 5,454,782 A | 10/1995 | Perkins |
| 5,456,667 A | 10/1995 | Ham et al. |
| 5,458,596 A | 10/1995 | Lax et al. |
| 5,465,717 A | 11/1995 | Imran et al. |
| 5,471,982 A | 12/1995 | Edwards et al. |
| 5,474,530 A | 12/1995 | Passafaro et al. |
| 5,478,309 A | 12/1995 | Sweezer et al. |
| 5,485,849 A | 1/1996 | Panescu et al. |
| 5,496,271 A | 3/1996 | Burton et al. |
| 5,496,311 A | 3/1996 | Abele et al. |
| 5,496,312 A | 3/1996 | Klicek |
| 5,500,011 A | 3/1996 | Desai |
| 5,505,728 A | 4/1996 | Ellman et al. |
| 5,505,730 A | 4/1996 | Edwards |
| 5,507,791 A | 4/1996 | Sit'ko |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,545,161 A | 8/1996 | Imran |
| 5,545,193 A | 8/1996 | Fleischman et al. |
| 5,547,469 A | 8/1996 | Rowland et al. |
| 5,549,559 A | 8/1996 | Eshel |
| 5,549,655 A | 8/1996 | Erickson |
| 5,549,661 A | 8/1996 | Kordis et al. |
| RE35,330 E | 9/1996 | Malone et al. |
| 5,558,073 A | 9/1996 | Pomeranz et al. |
| 5,562,608 A | 10/1996 | Sekins et al. |
| 5,571,074 A | 11/1996 | Buckman et al. |
| 5,571,088 A | 11/1996 | Lennox et al. |
| 5,574,059 A | 11/1996 | Regunathan et al. |
| 5,578,072 A | 11/1996 | Barone et al. |
| 5,582,609 A | 12/1996 | Swanson et al. |
| 5,588,432 A | 12/1996 | Crowley |
| 5,588,812 A | 12/1996 | Taylor et al. |
| 5,595,183 A | 1/1997 | Swanson et al. |
| 5,598,848 A | 2/1997 | Swanson et al. |
| 5,599,345 A | 2/1997 | Edwards et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,623,940 A | 4/1997 | Daikuzono |
| 5,624,439 A | 4/1997 | Edwards et al. |
| 5,626,618 A | 5/1997 | Ward et al. |
| 5,630,425 A | 5/1997 | Panescu et al. |
| 5,630,794 A | 5/1997 | Lax et al. |
| 5,634,471 A | 6/1997 | Fairfax et al. |
| 5,641,326 A | 6/1997 | Adams |
| 5,647,870 A | 7/1997 | Kordis et al. |
| 5,660,175 A | 8/1997 | Dayal |
| 5,678,535 A | 10/1997 | DiMarco |
| 5,680,860 A | 10/1997 | Imran |
| 5,681,280 A | 10/1997 | Rusk et al. |
| 5,681,308 A | 10/1997 | Edwards et al. |
| 5,687,723 A | 11/1997 | Avitall |
| 5,688,267 A | 11/1997 | Panescu et al. |
| 5,693,078 A | 12/1997 | Desai et al. |
| 5,694,934 A | 12/1997 | Edelman |
| 5,695,471 A | 12/1997 | Wampler |
| 5,699,799 A | 12/1997 | Xu et al. |
| 5,702,386 A | 12/1997 | Stern et al. |
| 5,707,218 A | 1/1998 | Maher et al. |
| 5,707,336 A | 1/1998 | Rubin |
| 5,707,352 A | 1/1998 | Sekins et al. |
| 5,722,401 A | 3/1998 | Pietroski et al. |
| 5,722,403 A | 3/1998 | McGee et al. |
| 5,722,416 A | 3/1998 | Swanson et al. |
| 5,725,525 A | 3/1998 | Kordis |
| 5,727,569 A | 3/1998 | Benetti et al. |
| 5,728,094 A | 3/1998 | Edwards |
| 5,730,128 A | 3/1998 | Pomeranz et al. |
| 5,730,704 A | 3/1998 | Avitall |
| 5,730,726 A | 3/1998 | Klingenstein |
| 5,730,741 A | 3/1998 | Horzewski et al. |
| 5,735,846 A | 4/1998 | Panescu et al. |
| 5,740,808 A | 4/1998 | Panescu et al. |
| 5,741,248 A | 4/1998 | Stern et al. |
| 5,752,518 A | 5/1998 | McGee et al. |
| 5,755,714 A | 5/1998 | Murphy-Chutorian |
| 5,755,715 A | 5/1998 | Stern et al. |
| 5,755,753 A | 5/1998 | Knowlton |
| 5,759,158 A | 6/1998 | Swanson |
| 5,765,568 A | 6/1998 | Sweezer et al. |
| 5,769,846 A | 6/1998 | Edwards et al. |
| 5,769,847 A | 6/1998 | Panescu et al. |
| 5,772,590 A | 6/1998 | Webster |
| 5,779,669 A | 7/1998 | Haissaguerre et al. |
| 5,779,698 A | 7/1998 | Clayman et al. |
| 5,782,239 A | 7/1998 | Webster |
| 5,782,797 A | 7/1998 | Schweich et al. |
| 5,782,827 A | 7/1998 | Gough et al. |
| 5,782,848 A | 7/1998 | Lennox |
| 5,782,899 A | 7/1998 | Imran |
| 5,792,064 A | 8/1998 | Panescu et al. |
| 5,795,303 A | 8/1998 | Swanson et al. |
| 5,800,375 A | 9/1998 | Sweezer et al. |
| 5,807,306 A | 9/1998 | Shapland et al. |
| 5,810,757 A | 9/1998 | Sweezer et al. |
| 5,810,807 A | 9/1998 | Ganz et al. |
| 5,817,028 A | 10/1998 | Anderson |
| 5,817,073 A | 10/1998 | Krespi |
| 5,820,554 A | 10/1998 | Davis et al. |
| 5,823,189 A | 10/1998 | Kordis |
| 5,827,277 A | 10/1998 | Edwards |
| 5,833,651 A | 11/1998 | Donovan et al. |
| 5,836,905 A | 11/1998 | Lemelson et al. |
| 5,836,947 A | 11/1998 | Fleischman et al. |
| 5,837,001 A | 11/1998 | Mackey |
| 5,843,075 A | 12/1998 | Taylor |
| 5,843,077 A | 12/1998 | Edwards |
| 5,846,238 A | 12/1998 | Jackson et al. |
| 5,848,969 A | 12/1998 | Panescu et al. |
| 5,848,972 A | 12/1998 | Triedman et al. |
| 5,849,026 A | 12/1998 | Zhou et al. |
| 5,855,577 A | 1/1999 | Murphy-Chutorian et al. |
| 5,860,974 A | 1/1999 | Abele |
| 5,863,291 A | 1/1999 | Schaer |
| 5,865,791 A | 2/1999 | Whayne et al. |
| 5,868,740 A | 2/1999 | LeVeen et al. |
| 5,871,443 A | 2/1999 | Edwards et al. |
| 5,871,523 A | 2/1999 | Fleischman et al. |
| 5,873,852 A | 2/1999 | Vigil et al. |
| 5,873,865 A | 2/1999 | Horzewski et al. |
| 5,876,340 A | 3/1999 | Tu et al. |
| 5,876,399 A | 3/1999 | Chia et al. |
| 5,881,727 A | 3/1999 | Edwards |
| 5,882,346 A | 3/1999 | Pomeranz et al. |
| 5,891,135 A | 4/1999 | Jackson et al. |
| 5,891,136 A | 4/1999 | McGee et al. |
| 5,891,138 A | 4/1999 | Tu et al. |
| 5,893,847 A | 4/1999 | Kordis |
| 5,897,554 A | 4/1999 | Chia et al. |
| 5,899,882 A | 5/1999 | Waksman et al. |
| 5,904,651 A | 5/1999 | Swanson et al. |
| 5,904,711 A | 5/1999 | Flom et al. |
| 5,906,636 A | 5/1999 | Casscells, III et al. |
| 5,908,445 A | 6/1999 | Whayne et al. |
| 5,908,446 A | 6/1999 | Imran |
| 5,908,839 A | 6/1999 | Levitt et al. |
| 5,911,218 A | 6/1999 | DiMarco |
| 5,916,235 A | 6/1999 | Guglielmi |

(56) References Cited

U.S. PATENT DOCUMENTS

| | | |
|---|---|---|
| 5,919,147 A | 7/1999 | Jain |
| 5,919,172 A | 7/1999 | Golba |
| 5,924,424 A | 7/1999 | Stevens et al. |
| 5,928,228 A | 7/1999 | Kordis et al. |
| 5,931,835 A | 8/1999 | Mackey |
| 5,935,079 A | 8/1999 | Swanson et al. |
| 5,941,869 A | 8/1999 | Patterson et al. |
| 5,951,494 A | 9/1999 | Wang et al. |
| 5,951,546 A | 9/1999 | Lorentzen |
| 5,954,661 A | 9/1999 | Greenspon et al. |
| 5,954,662 A | 9/1999 | Swanson et al. |
| 5,954,717 A | 9/1999 | Behl et al. |
| 5,957,920 A | 9/1999 | Baker |
| 5,957,961 A | 9/1999 | Maguire et al. |
| 5,964,753 A | 10/1999 | Edwards |
| 5,964,796 A | 10/1999 | Imran |
| 5,971,983 A | 10/1999 | Lesh |
| 5,972,026 A | 10/1999 | Laufer et al. |
| 5,976,175 A | 11/1999 | Hirano et al. |
| 5,976,709 A | 11/1999 | Kageyama et al. |
| 5,979,456 A | 11/1999 | Magovern |
| 5,980,563 A | 11/1999 | Tu et al. |
| 5,984,917 A | 11/1999 | Fleischman et al. |
| 5,984,971 A | 11/1999 | Faccioli et al. |
| 5,991,650 A | 11/1999 | Swanson et al. |
| 5,992,419 A | 11/1999 | Sterzer et al. |
| 5,993,462 A | 11/1999 | Pomeranz et al. |
| 5,997,534 A | 12/1999 | Tu et al. |
| 5,999,855 A | 12/1999 | DiMarco |
| 6,001,054 A | 12/1999 | Regulla et al. |
| 6,003,517 A | 12/1999 | Sheffield et al. |
| 6,004,269 A | 12/1999 | Crowley et al. |
| 6,006,755 A | 12/1999 | Edwards |
| 6,008,211 A | 12/1999 | Robinson et al. |
| 6,009,877 A | 1/2000 | Edwards |
| 6,010,500 A | 1/2000 | Sherman et al. |
| 6,014,579 A | 1/2000 | Pomeranz et al. |
| 6,016,437 A | 1/2000 | Tu et al. |
| 6,019,757 A * | 2/2000 | Scheldrup ......... A61B 17/12109 606/135 |
| 6,023,638 A | 2/2000 | Swanson |
| 6,024,740 A | 2/2000 | Lesh et al. |
| 6,029,091 A | 2/2000 | De La Rama et al. |
| 6,033,397 A | 3/2000 | Laufer et al. |
| 6,036,687 A | 3/2000 | Laufer et al. |
| 6,036,689 A | 3/2000 | Tu et al. |
| 6,039,731 A | 3/2000 | Taylor et al. |
| 6,045,549 A | 4/2000 | Smethers et al. |
| 6,045,550 A | 4/2000 | Simpson et al. |
| 6,050,992 A | 4/2000 | Nichols |
| 6,053,172 A | 4/2000 | Hovda et al. |
| 6,053,909 A | 4/2000 | Shadduck |
| 6,056,744 A | 5/2000 | Edwards |
| 6,056,769 A | 5/2000 | Epstein et al. |
| 6,063,078 A | 5/2000 | Wittkampf |
| 6,071,280 A | 6/2000 | Edwards et al. |
| 6,071,281 A | 6/2000 | Burnside et al. |
| 6,071,282 A | 6/2000 | Fleischman |
| 6,083,255 A | 7/2000 | Laufer et al. |
| 6,090,104 A | 7/2000 | Webster |
| 6,092,528 A | 7/2000 | Edwards |
| 6,102,886 A | 8/2000 | Lundquist et al. |
| 6,106,524 A | 8/2000 | Eggers et al. |
| 6,123,702 A | 9/2000 | Swanson et al. |
| 6,123,703 A | 9/2000 | Tu et al. |
| 6,139,527 A | 10/2000 | Laufer et al. |
| 6,139,571 A | 10/2000 | Fuller et al. |
| 6,142,993 A | 11/2000 | Whayne et al. |
| 6,143,013 A | 11/2000 | Samson et al. |
| 6,149,647 A | 11/2000 | Tu et al. |
| 6,152,143 A | 11/2000 | Edwards |
| 6,152,899 A | 11/2000 | Farley et al. |
| 6,159,194 A | 12/2000 | Eggers et al. |
| 6,179,833 B1 | 1/2001 | Taylor |
| 6,183,468 B1 | 2/2001 | Swanson et al. |
| 6,198,970 B1 | 3/2001 | Freed et al. |
| 6,200,311 B1 | 3/2001 | Danek et al. |
| 6,200,332 B1 | 3/2001 | Del Giglio |
| 6,200,333 B1 | 3/2001 | Laufer |
| 6,210,367 B1 | 4/2001 | Carr |
| 6,212,433 B1 | 4/2001 | Behl |
| 6,214,002 B1 | 4/2001 | Fleischman et al. |
| 6,216,043 B1 | 4/2001 | Swanson et al. |
| 6,216,044 B1 | 4/2001 | Kordis |
| 6,217,576 B1 | 4/2001 | Tu et al. |
| 6,235,024 B1 | 5/2001 | Tu |
| 6,241,727 B1 | 6/2001 | Tu et al. |
| 6,245,065 B1 | 6/2001 | Panescu et al. |
| 6,254,598 B1 | 7/2001 | Edwards et al. |
| 6,258,087 B1 | 7/2001 | Edwards et al. |
| 6,264,653 B1 | 7/2001 | Falwell |
| 6,269,813 B1 | 8/2001 | Fitzgerald et al. |
| 6,270,476 B1 | 8/2001 | Santoianni et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,304 B1 | 9/2001 | Eggers et al. |
| 6,296,639 B1 | 10/2001 | Truckai et al. |
| 6,299,633 B1 | 10/2001 | Laufer |
| 6,322,559 B1 | 11/2001 | Daulton et al. |
| 6,322,584 B2 | 11/2001 | Ingle et al. |
| 6,338,727 B1 | 1/2002 | Noda et al. |
| 6,338,836 B1 | 1/2002 | Kuth et al. |
| 6,346,104 B2 | 2/2002 | Daly et al. |
| 6,355,031 B1 | 3/2002 | Edwards et al. |
| 6,379,352 B1 | 4/2002 | Reynolds et al. |
| 6,409,723 B1 | 6/2002 | Edwards |
| 6,411,852 B1 | 6/2002 | Danek et al. |
| 6,416,511 B1 | 7/2002 | Lesh et al. |
| 6,416,740 B1 | 7/2002 | Unger |
| 6,423,105 B1 | 7/2002 | Iijima et al. |
| 6,425,895 B1 | 7/2002 | Swanson et al. |
| 6,440,129 B1 | 8/2002 | Simpson |
| 6,442,435 B2 | 8/2002 | King et al. |
| 6,458,121 B1 | 10/2002 | Rosenstock et al. |
| 6,460,545 B2 | 10/2002 | Kordis |
| 6,488,673 B1 | 12/2002 | Laufer et al. |
| 6,488,679 B1 | 12/2002 | Swanson et al. |
| 6,493,589 B1 | 12/2002 | Medhkour et al. |
| 6,494,880 B1 | 12/2002 | Swanson et al. |
| 6,496,738 B2 | 12/2002 | Carr |
| 6,514,246 B1 | 2/2003 | Swanson et al. |
| 6,526,320 B2 | 2/2003 | Mitchell |
| 6,529,756 B1 | 3/2003 | Phan et al. |
| 6,544,226 B1 | 4/2003 | Gaiser et al. |
| 6,544,262 B2 | 4/2003 | Fleischman |
| 6,547,788 B1 | 4/2003 | Maguire et al. |
| 6,558,378 B2 | 5/2003 | Sherman et al. |
| 6,572,612 B2 | 6/2003 | Stewart et al. |
| 6,575,623 B2 | 6/2003 | Werneth |
| 6,575,969 B1 | 6/2003 | Rittman, III et al. |
| 6,582,427 B1 | 6/2003 | Goble et al. |
| 6,582,430 B2 | 6/2003 | Hall |
| 6,589,235 B2 | 7/2003 | Wong et al. |
| 6,610,054 B1 | 8/2003 | Edwards et al. |
| 6,620,159 B2 | 9/2003 | Hegde |
| 6,626,903 B2 | 9/2003 | McGuckin et al. |
| 6,634,363 B1 | 10/2003 | Danek et al. |
| 6,635,056 B2 | 10/2003 | Kadhiresan et al. |
| 6,638,273 B1 | 10/2003 | Farley et al. |
| 6,640,120 B1 | 10/2003 | Swanson et al. |
| 6,645,200 B1 | 11/2003 | Koblish et al. |
| 6,652,548 B2 | 11/2003 | Evans et al. |
| 6,669,693 B2 | 12/2003 | Friedman |
| 6,673,068 B1 | 1/2004 | Berube |
| 6,692,492 B2 | 2/2004 | Simpson et al. |
| 6,699,243 B2 | 3/2004 | West et al. |
| 6,714,822 B2 | 3/2004 | King et al. |
| 6,723,091 B2 | 4/2004 | Goble et al. |
| 6,743,197 B1 | 6/2004 | Edwards |
| 6,749,604 B1 | 6/2004 | Eggers et al. |
| 6,749,606 B2 | 6/2004 | Keast et al. |
| 6,767,347 B2 | 7/2004 | Sharkey et al. |
| 6,770,070 B1 | 8/2004 | Balbierz |

(56) References Cited

U.S. PATENT DOCUMENTS

| | | | |
|---|---|---|---|
| 6,802,843 B2 | 10/2004 | Truckai et al. |
| 6,805,131 B2 | 10/2004 | Kordis |
| 6,837,888 B2 | 1/2005 | Ciarrocca et al. |
| 6,840,243 B2 | 1/2005 | Deem et al. |
| 6,849,073 B2 | 2/2005 | Hoey et al. |
| 6,852,091 B2 | 2/2005 | Edwards et al. |
| 6,852,110 B2 | 2/2005 | Roy et al. |
| 6,866,662 B2 | 3/2005 | Fuimaono et al. |
| 6,881,213 B2 | 4/2005 | Ryan et al. |
| 6,893,436 B2 | 5/2005 | Woodard et al. |
| 6,893,439 B2 | 5/2005 | Fleischman |
| 6,895,267 B2 | 5/2005 | Panescu et al. |
| 6,904,303 B2 | 6/2005 | Phan et al. |
| 6,917,834 B2 | 7/2005 | Koblish et al. |
| 6,939,346 B2 | 9/2005 | Kannenberg et al. |
| 6,954,977 B2 | 10/2005 | Maguire et al. |
| 7,027,869 B2 | 4/2006 | Danek et al. |
| 7,043,307 B1 | 5/2006 | Zelickson et al. |
| 7,104,987 B2 | 9/2006 | Biggs et al. |
| 7,104,990 B2 | 9/2006 | Jenkins et al. |
| 7,118,568 B2 | 10/2006 | Hassett et al. |
| 7,122,033 B2 | 10/2006 | Wood |
| 7,131,445 B2 | 11/2006 | Amoah |
| 7,186,251 B2 | 3/2007 | Malecki et al. |
| 7,198,635 B2 | 4/2007 | Danek et al. |
| 7,200,445 B1 | 4/2007 | Dalbec et al. |
| 7,241,295 B2 | 7/2007 | Maguire |
| 7,255,693 B1 | 8/2007 | Johnston et al. |
| 7,264,002 B2 | 9/2007 | Danek et al. |
| 7,266,414 B2 | 9/2007 | Cornelius et al. |
| 7,273,055 B2 | 9/2007 | Danek et al. |
| 7,425,212 B1 | 9/2008 | Danek et al. |
| 7,542,802 B2 | 6/2009 | Danek et al. |
| 7,556,624 B2 | 7/2009 | Laufer et al. |
| 7,740,017 B2 | 6/2010 | Danek et al. |
| 2003/0050631 A1 | 3/2003 | Mody et al. |
| 2003/0065371 A1 | 4/2003 | Satake |
| 2003/0069570 A1 | 4/2003 | Witzel et al. |
| 2003/0187430 A1 | 10/2003 | Vorisek |
| 2003/0236455 A1 | 12/2003 | Swanson et al. |
| 2004/0153056 A1 | 8/2004 | Muller et al. |
| 2004/0249401 A1 | 12/2004 | Rabiner et al. |
| 2005/0010270 A1 | 1/2005 | Laufer |
| 2005/0096644 A1 | 5/2005 | Hall et al. |
| 2005/0171396 A1 | 8/2005 | Pankratov et al. |
| 2005/0193279 A1 | 9/2005 | Daners |
| 2005/0203503 A1 | 9/2005 | Edwards et al. |
| 2005/0240176 A1 | 10/2005 | Oral et al. |
| 2005/0251128 A1 | 11/2005 | Amoah |
| 2006/0062808 A1 | 3/2006 | Laufer et al. |
| 2006/0079887 A1 | 4/2006 | Buysse et al. |
| 2006/0089637 A1 | 4/2006 | Werneth et al. |
| 2006/0135953 A1 | 6/2006 | Kania et al. |
| 2006/0137698 A1 | 6/2006 | Danek et al. |
| 2006/0247617 A1 | 11/2006 | Danek et al. |
| 2006/0247618 A1 | 11/2006 | Kaplan et al. |
| 2006/0247619 A1 | 11/2006 | Kaplan et al. |
| 2006/0247727 A1 | 11/2006 | Biggs et al. |
| 2006/0247746 A1 | 11/2006 | Danek et al. |
| 2006/0254600 A1 | 11/2006 | Danek et al. |
| 2006/0278243 A1 | 12/2006 | Danek et al. |
| 2006/0278244 A1 | 12/2006 | Danek et al. |
| 2006/0282071 A1 | 12/2006 | Utley et al. |
| 2007/0074719 A1 | 4/2007 | Danek et al. |
| 2007/0083194 A1 | 4/2007 | Kunis et al. |
| 2007/0083197 A1 | 4/2007 | Danek et al. |
| 2007/0100390 A1 | 5/2007 | Danaek et al. |
| 2007/0102011 A1 | 5/2007 | Danek et al. |
| 2007/0106292 A1 | 5/2007 | Kaplan et al. |
| 2007/0106296 A1 | 5/2007 | Laufer et al. |
| 2007/0106348 A1 | 5/2007 | Laufer |
| 2007/0118184 A1 | 5/2007 | Danek et al. |
| 2007/0118190 A1 | 5/2007 | Danek et al. |
| 2007/0123958 A1 | 5/2007 | Laufer |
| 2007/0123961 A1 | 5/2007 | Danek et al. |
| 2007/0129720 A1 | 6/2007 | Demarais et al. |
| 2008/0004596 A1 | 1/2008 | Yun et al. |
| 2008/0097424 A1 | 4/2008 | Wizeman et al. |
| 2008/0255642 A1 | 10/2008 | Zarins et al. |
| 2009/0018538 A1 | 1/2009 | Webster et al. |
| 2009/0030477 A1 | 1/2009 | Jarrard |
| 2009/0043301 A1 | 2/2009 | Jarrard et al. |
| 2009/0069797 A1 | 3/2009 | Danek et al. |
| 2009/0112203 A1 | 4/2009 | Danek et al. |
| 2009/0143705 A1 | 6/2009 | Danek et al. |
| 2009/0143776 A1 | 6/2009 | Danek et al. |
| 2009/0192505 A1 | 7/2009 | Askew et al. |
| 2009/0192508 A1 | 7/2009 | Laufer et al. |
| 2009/0306644 A1 | 12/2009 | Mayse et al. |
| 2010/0160906 A1 | 6/2010 | Jarrard |
| 2010/0168727 A1* | 7/2010 | Hancock ............... A61B 18/18 606/33 |
| 2010/0185190 A1 | 7/2010 | Danek et al. |
| 2010/0204689 A1 | 8/2010 | Danek et al. |

FOREIGN PATENT DOCUMENTS

| | | |
|---|---|---|
| EP | 280225 A3 | 3/1989 |
| EP | 286145 A3 | 10/1990 |
| EP | 282225 B1 | 6/1992 |
| EP | 0 752 235 A1 | 1/1997 |
| EP | 0908150 A1 | 4/1999 |
| EP | 908713 A1 | 4/1999 |
| EP | 1 080 694 A1 | 3/2001 |
| EP | 768091 B1 | 7/2003 |
| EP | 1297795 B1 | 8/2005 |
| EP | 2 316 369 A1 | 5/2011 |
| FR | 2659240 B1 | 7/1997 |
| GB | 2233293 A | 1/1991 |
| GB | 2233293 B | 2/1994 |
| JP | 59167707 A2 | 9/1984 |
| JP | 7289557 A | 11/1995 |
| JP | 9047518 A2 | 2/1997 |
| JP | 9243837 A2 | 9/1997 |
| JP | 10026709 A2 | 1/1998 |
| RU | 2053814 C1 | 2/1996 |
| RU | 2091054 C1 | 9/1997 |
| SU | 545358 T | 2/1977 |
| WO | WO-8911311 A1 | 11/1989 |
| WO | WO-9502370 A2 | 1/1995 |
| WO | WO-9510322 A1 | 4/1995 |
| WO | WO-9604860 A1 | 2/1996 |
| WO | WO-9610961 A1 | 4/1996 |
| WO | WO-9732532 A1 | 9/1997 |
| WO | WO-9733715 A1 | 9/1997 |
| WO | WO-9737715 A1 | 10/1997 |
| WO | WO-9740751 A1 | 11/1997 |
| WO | WO-9844854 A1 | 10/1998 |
| WO | WO-9852480 A1 | 11/1998 |
| WO | WO-9856234 A1 | 12/1998 |
| WO | WO-9856324 A1 | 12/1998 |
| WO | WO-9858681 A2 | 12/1998 |
| WO | WO-9903413 A1 | 1/1999 |
| WO | WO-9913779 A2 | 3/1999 |
| WO | WO-9932040 A1 | 7/1999 |
| WO | WO-9934741 A1 | 7/1999 |
| WO | WO-9944506 A1 | 9/1999 |
| WO | WO-9945855 A1 | 9/1999 |
| WO | WO-9964109 A1 | 12/1999 |
| WO | WO-0051510 A1 | 9/2000 |
| WO | WO-0062699 A2 | 10/2000 |
| WO | WO-0103642 A1 | 1/2001 |
| WO | WO-0232333 A1 | 4/2002 |
| WO | WO-0232334 A1 | 4/2002 |
| WO | WO-2009082433 A2 | 7/2009 |
| WO | WO-2009137819 A1 | 11/2009 |
| WO | WO 2010/056848 | 5/2010 |

OTHER PUBLICATIONS

International Search Report for corresponding international application PCT/US2013/041332, dated Aug. 6, 2013, 16 pages.

An S.S., et al., "Airway Smooth Muscle Dynamics: A Common (56) References Cited

OTHER PUBLICATIONS

Pathway of Airway Obstruction in Asthma," European Respiratory Journal, 2007, 29 (5), 834-860.
Bel E.H., ""Hot stuff": Bronchial Thermoplasty for Asthma," American Journal of Respiratory and Critical Care Medicine, 2006, 173 (9), 941-943.
Brown R.H., et al., "Effect of Bronchial Thermoplasty on Airway Distensibility," European Respiratory Journal, 2005, 26 (2), 277-282.
Brown R.H., et al., "In Vivo evaluation of the Effectiveness of Bronchial Thermoplasty with Computed Tomography," Journal of Applied Physiology, 2005, 98 (5), 1603-1606.
Chhajed P.N., et al., "Will there be a Role for Bronchoscopic Radiofrequency Ablation", Journal of Bronchology, 2005, 12 (3), 184-186.
Abandoned U.S. Appl. No. 09/095,323, filed Jun. 10, 1998; now U.S. Pat. No. 7,264,002 dated Sep. 14, 2007.
Abandoned U.S. Appl. No. 09/244,173, filed Feb. 4, 1999; now U.S. Pat. No. 6,411,853 dated Jun. 25, 2002.
Cox G., et al., "Asthma Control during the Year after Bronchial Thermoplasty," New England journal of medicine, 2007, 356 (13), 1327-1337.
Cox G., et al., "Asthma Intervention Research (AIR) Trial Evaluating Bronchial Thermoplasty: Early Results," American Thoracic Society Annual Meeting, 2002, 1 page.
Cox G., et al., "Bronchial Thermoplasty for Asthma," American Journal of Respiratory and Critical Care Medicine, 2006, 173 (9), 965-969.
Cox G., et al., "Bronchial Thermoplasty: Long-Term Follow-Up and Patient Satisfaction," Chest, 2004, 126 (4), 822s.
Cox G., et al., "Bronchial Thermoplasty: One-Year Update, American Thoracic Society Annual Meeting," American Journal of Respiratory and Critical Care Medicine, 2004, 169, A313.
Cox G., et al., "Clinical Experience with Bronchial Thermoplasty for the Treatment of Asthma," Chest, 2003, 124, 106S.
Cox G., et al., "Development of a Novel Bronchoscopic Therapy for Asthma," Journal of Allergy and Clinical Immunology, 2003, 113 (2), S33.
Cox G., et al., "Early Clinical Experience with Bronchial Thermoplasty for the Treatment of Asthma," American Thoracic Society Annual Meeting, 2002, 1068.
Cox G., et al., "Impact of Bronchial Thermoplasty on Asthma Status: Interim Results from the Air Trial," 2006, 1 page.
Cox G., et al., "Radiofrequency Ablation of Airway Smooth Muscle for Sustained Treatment of Asthma: Preliminary Investigations," European Respiratory Journal, 2004, 24 (4), 659-663.
Danek C.J., et al., "Bronchial Thermoplasty Reduces Canine Airway Responsiveness to Local Methacholine Challenge," American Thoracic Society Annual Meeting, 2002, 1 page.
Danek C.J., et al., "Reduction in Airway Hyperresponsiveness to Methacholine by the Application of RF Energy in Dogs," Journal of Applied Physiology, 2004, 97 (5), 1946-1953.
Dierkesmann R., "Indication and Results of Endobronchial Laser Therapy," Lung, 1990, 168, 1095-1102.
Hogg J. C., "The Pathology of Asthma," APMIS, 1997, 105 (10), 735-745.
International Search Report for Application No. PCT/US00/05412, dated Jun. 20, 2000, 2 pages.
International Search Report for Application No. PCT/US00/18197, dated Oct. 3, 2000, 1 pages.
International Search Report for Application No. PCT/US00/28745, dated Mar. 28, 2001, 6 pages.
International Search Report for Application No. PCT/US01/32321, dated Jan. 18, 2002, 2 pages.
International Search Report for Application No. PCT/US98/03759, dated Jul. 30, 1998, 1 page.
International Search Report for Application No. PCT/US98/26227, dated Mar. 25, 1999, 1 page.
International Search Report for Application No. PCT/US99/00232, dated Mar. 4, 1999, 1 page.
International Search Report for Application No. PCT/US99/12986, dated Sep. 29, 1999, 1 page.
Ivanyuta O.M., et al., "Effect of Low-Power Laser Irradiation of Bronchial Mucosa on the State of Systemic and Local Immunity in Patients with Chronic Bronchitis," Problemy Tuberkuleza, 1991, 6, 26-29.
James A.L., et al., "The Mechanics of Airway Narrowing in Asthma," American Review of Respiratory Diseases, 1989, 139 (1), 242-246.
Johnson S. R., et al., "Synthetic Functions of Airway Smooth Muscle in Asthma," Trends Pharmacol. Sci., 1997, 18 (8), 288-292.
Kitamura S., "Color Atlas of Clinical Application of Fiberoptic Bronchoscopy," 1990, Year Book Medical Publishers, 2 pages.
Laviolette M., et al., "Asthma Intervention Research (Air) Trial: Early Safety Assessment of Bronchial Thermoplasty," American Journal of Respiratory and Critical Care Medicine, 2004, 169, A314.
Leff A., et al., "Bronchial Thermoplasty Alters Airway Smooth Muscle and Reduces Responsiveness in Dogs: A Possible Procedure for the Treatment of Asthma," American Thoracic Society Annual Meeting, 2002, 1 page.
Lim E.C., et al., "Botulinum Toxin: A Novel Therapeutic Option for Bronchial Asthma", Medical Hypotheses, 2006, 66 (5), 915-919.
Lombard C.M., et al., "Histologic Effects of Bronchial Thermoplasty of Canine and Human Airways,"American Thoracic Society Annual Meeting, 2002, 1 page.
Macklem P. T., "Mechanical Factors Determining Maximum Bronchoconstriction," European Respiratory Journal, 1989, 6, 516s-519s.
Mayse M.L., et al., "Clinical Pearls for Bronchial Thermoplasty," Journal of Bronchology, 2007, 14 (2), 115-123.
Miller J.D., et al., "A Prospective Feasibility Study of Bronchial Thermoplasty in the Human Airway," Chest, 2005, 127 (6), 1999-2006.
Miller J.D., et al., "Bronchial Thermoplasty is Well Tolerated by Non-Asthmatic Patients Requiring Lobectomy," American Thoracic Society Annual Meeting, 2002, 1 page.
Mitzner W., "Airway Smooth Muscle the Appendix of the Lung," American Journal of Respiratory and Critical Care Medicine, 2004, 169 (7), 787-790.
Netter F.H., "Respiratory System: A Compilation of Paintings Depicting Anatomy and Embryology, Physiology, Pathology, Pathophysiology, and Clinical Features and Treatment of Diseases,In The CIBA Collection of Medical Illustrations M.B. Divertie, ed., Summit: New Jerse," 1979, 7, 119-135.
Notice of final Rejection, Japanese Patent Application No. 2000-553172, dated Sep. 2, 2008, 5 pages.
Provotorov V.M., et al., "The Clinical Efficacy of Treating Patients with Nonspecific Lung Diseases Using Low-energy Laser Irradiation and Intrapulmonary Drug Administration," Terapevticheskii Arkhiv, 1991, 62 (12), 18-23.
Rubin A., et al., "Bronchial Thermoplasty Improves Asthma Status of Moderate to Severe Perisstent Asthmatics Over and Above Current Standard-of-Care," American College of Chest Physicians, 2006, 2 pages.
Shesterina M.V., et al., "Effect of Laser Therapy on Immunity in Patients with Bronchial Asthma and Pulmonary Tuberculosis," Problemy Tuberkuleza, 1994, 5, 23-26.
Solway J., et al., "Airway Smooth Muscle as a Target for Asthma Therapy," New England Journal of medicine, 2007, 356 (13), 1367-1369.
Sterk P.J., et al., "Heterogeneity of Airway Hyperresponsiveness: Time for Unconventional, But Traditional, Studies," Journal of Applied Physiology, 2004, 96 (6), 2017-2018.
Toma T.P., et al., "Brave New World for Interventional Bronchoscopy," Thorax, 2005, 60 (3), 180-181.
Trow T.K., "Clinical Year in Review I: Diagnostic Imaging, Asthma, Lung Transplantation, and Interventional Pulmonology," Proceedings of the American Thoracic Society, 2006, 3 (7), 553-556.
Vasilotta P.L., et al., "I-R Laser: A New Therapy in Rhino-Sino-Nasal Bronchial Syndrome with Asthmatic Component," American Society for Laser Medicine and Surgery Abstracts, 74. 1993.

(56) References Cited

OTHER PUBLICATIONS

Vorotnev A.I., et al., "The Treatment of Patients with Chronic Obstructive Bronchitis by Using a Low-power Laser at a General Rehabilitation Center," Terapevticheskii Arkhiv, 1997, 69 (3), 17-19.
Wiggs B.R., et al., "On the Mechanism of Mucosal Folding in Normal and Asthmatic Airways," Journal of Applied Physiology, 1997, 83 (6), 1814-1821.
Wilson S.R., et al., "Global Assessment after Bronchial Thermoplasty: The Patients Perspective," Journal of Outcomes Research, 2006, 10, 37-46.
Wizeman W., et al., "A Computer Model of Thermal Treatment of Airways by Radiofrequency (RF) Energy Delivery," American Thoracic Society Annual Meeting, 2007, 1 page.

* cited by examiner

SYSTEMS AND METHODS FOR TREATING TISSUE OF A PASSAGEWAY WITHIN A BODY

CROSS-REFERENCE TO RELATED APPLICATIONS

This application claims the benefit of priority from U.S. Provisional Application No. 61/655,229 filed on Jun. 4, 2012, the entirety of which is incorporated by reference herein.

FIELD OF THE INVENTION

The embodiments described herein relate to systems and methods for treating tissue of a passageway within a body. In particular, embodiments of the present disclosure relate to systems and methods for treating tissue by delivering energy to tissue of a passageway within a body and monitoring tissue treatment by, for example, using a reflected portion of the energy delivered to the tissue during the tissue treatment procedure.

BACKGROUND OF THE INVENTION

The anatomy of a lung includes multiple airways. As a result of certain genetic and/or environmental conditions, an airway may become fully or partially obstructed, resulting in an airway disease such as emphysema, bronchitis, chronic obstructive pulmonary disease (COPD), and asthma. Certain obstructive airway diseases, including, but not limited to, COPD and asthma, are reversible. Treatments have accordingly been designed in order to reverse the obstruction of airways caused by these diseases.

One treatment option includes management of the obstructive airway diseases via pharmaceuticals. For example, in a patient with asthma, inflammation and swelling of the airways may be reversed through the use of short-acting bronchodilators, long-acting bronchodilators, and/or anti-inflammatories. Pharmaceuticals, however, are not always a desirable treatment option because in many cases they do not produce permanent results.

Accordingly, more permanent/longer-lasting treatment options have been developed in the form of energy delivery systems for reversing obstruction of airways. Such systems may include a delivery device having an energy emitting portion including one or more energy conducting elements. The one or more energy conducting elements may be designed to contact an airway of a lung to deliver energy at a desired intensity for a period of time that allows for the smooth muscle tissue of the airway to be altered and/or ablated.

Some systems may control tissue treatment by monitoring one or more parameters of the tissue. For example, some systems may additionally include one or more thermocouples that continuously or intermittently monitor the temperature of the treated tissue. When the temperature of the tissue is raised beyond a temperature threshold, the treatment may be terminated.

These systems, while effective for their intended purpose, may not prevent overtreatment during the treatment procedure (i.e., treatment of adjacent tissue and/or anatomical structures). Indeed, these systems may resume treatment of the targeted tissue after the temperature of the tissue drops below a threshold temperature when the tissue has been sufficiently altered and/or ablated.

Furthermore, the one or more thermocouples may add to the overall cost of manufacturing the energy delivery devices. While the cost may be less of an issue with reusable energy delivery devices where the cost can be amortized due to repeated usage, this cost may be high in the case of disposable energy delivery devices.

Therefore, there is a need for alternative systems and methods for treating tissue and monitoring tissue treatment.

SUMMARY OF THE INVENTION

Embodiments of the present invention are directed to systems and methods for treating tissue in a passageway within a body.

One embodiment of the disclosure is directed to a method for treating tissue in a passageway within a body. The method may include positioning a medical device adjacent a treatment site in the passageway. The medical device may include an elongate member having a proximal end and a distal end, and an energy emitting portion adjacent the distal end. The method may further include supplying an amount of energy from an energy source to the energy emitting portion to treat tissue at the treatment site. A first portion of the amount of energy may be transmitted through the energy emitting portion to the tissue and a second portion of the amount of energy may be reflected back towards the proximal end of the elongate member. The method may also include monitoring a signal corresponding to one of the first portion of the amount of energy transmitted to the tissue and the second portion of the amount of energy reflected back from the tissue.

In various embodiments, the device may include one or more of the following additional features: wherein the signal corresponds to the first portion of the amount of energy, the signal has a power, and wherein the power decreases during delivery of energy to the tissue; wherein the signal corresponds to the second portion of the amount of energy, the signal has a power, and wherein the power increases during delivery of energy to the tissue; wherein the monitoring includes measuring a rate of change of the power; further including determining whether a change in the rate of change of the power passes a threshold value, and further including terminating the supply of energy from the energy source when the change in the rate of change of the power falls under the threshold value; wherein the energy source is an RF generator.

Another embodiment of the disclosure is directed to a method for treating tissue in a passageway within a body. The method may include positioning a medical device at a treatment site in the passageway. The medical device may include an elongate member having a proximal end and a distal end, and an energy emitting portion adjacent the distal end. The method may further include supplying an amount of energy from an energy source to the energy emitting portion to treat tissue at the treatment site. A first portion of the amount of energy may be transmitted through the energy emitting portion to the tissue and a second portion of the amount of energy may be reflected back towards the proximal end of the elongate member. The method may also include detecting a signal corresponding to the reflected energy and determining a state of treatment based on the signal.

In various embodiments, the device may include one or more of the following additional features: wherein the detecting is performed by a bi-directional coupler; wherein the signal has a power, and wherein the method further includes determining if the power passes a threshold;

wherein the method further includes terminating the supply of energy to the energy emitting portion when the power exceeds the threshold; wherein the threshold corresponds to a power level for ablating or otherwise altering tissue; wherein the signal corresponding to the reflected energy has a power, and wherein the power is proportional to the impedance of the tissue; wherein the impedance of the tissue decreases during delivery of energy to the tissue; and wherein the energy source is an RF generator; wherein the signal corresponding to the reflected energy has a power, and wherein the power is a function of the amount of tissue contact; further including analyzing the signal to determine a rate of change in the signal, and determining the amount of contact based on the rate of change; further including expanding the energy emitting portion from a collapsed configuration to an expanded configuration to contact tissue; wherein the signal corresponding to the reflected energy has a power, and wherein the power is configured to change as the energy emitting contacts tissue; and wherein the energy source is an RF generator.

Another embodiment is directed to system for treating tissue of a passageway within a body. The system may include an energy source, a medical device for delivering energy to a treatment site in the passageway within the body. The medical device may include an elongate member having a proximal end and a distal end. The medical device may be configured to receive an amount of energy from the energy source. A first portion of the amount of energy may be transmitted through the distal end to tissue at the treatment site and a second portion of the amount of energy may be reflected back towards the proximal end of the elongate member. The system may also include a dual directional coupler coupled to the medical device, the dual directional coupler may be configured to detect a signal corresponding to one or both of the first portion of the amount of energy and the second portion of the amount of energy. The system may also include a controller that may be configured to analyze the signal to determine the state of treatment.

In various embodiments, the system may include one or more of the following features: wherein the signal may correspond to the second portion of the amount of energy, the signal may have a power having a magnitude which may increase during delivery of energy to the tissue, and the controller may be configured to terminate the supply of energy from the energy source when the change in the rate of change of the power falls under a threshold value.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Reference will now be made in detail to exemplary embodiments of the invention, examples of which are illustrated in the accompanying drawings. Whenever possible, the same reference numbers will be used throughout the drawings to refer to same or like parts.

Generally described, the present disclosure relates to systems and methods for treating tissue by delivering energy to tissue within the wall of a passageway in a patient's body and monitoring tissue treatment. "Passageway" as used herein refers to and includes any cavity, lumen, space, or like within the body. More particularly, embodiments of the present disclosure relate to systems and methods for delivering energy to tissue, such as airway smooth muscle tissue, nerve tissue, or other structures, in the airway of a lung in order to treat reversible obstructive airway diseases including, but not limited to, COPD and asthma. Embodiments of the present disclosure further include monitoring the effects of the treatment on one or more characteristics of the tissue. It is contemplated that the disclosed systems and methods may also be utilized to deliver energy to tissue located in the heart, bile ducts, urinary system, gastrointestinal system (e.g., liver cancer), or for other applications within the lung (e.g., lung cancer), and monitor the effects of the treatment on the tissue of those systems.

Figure 1:
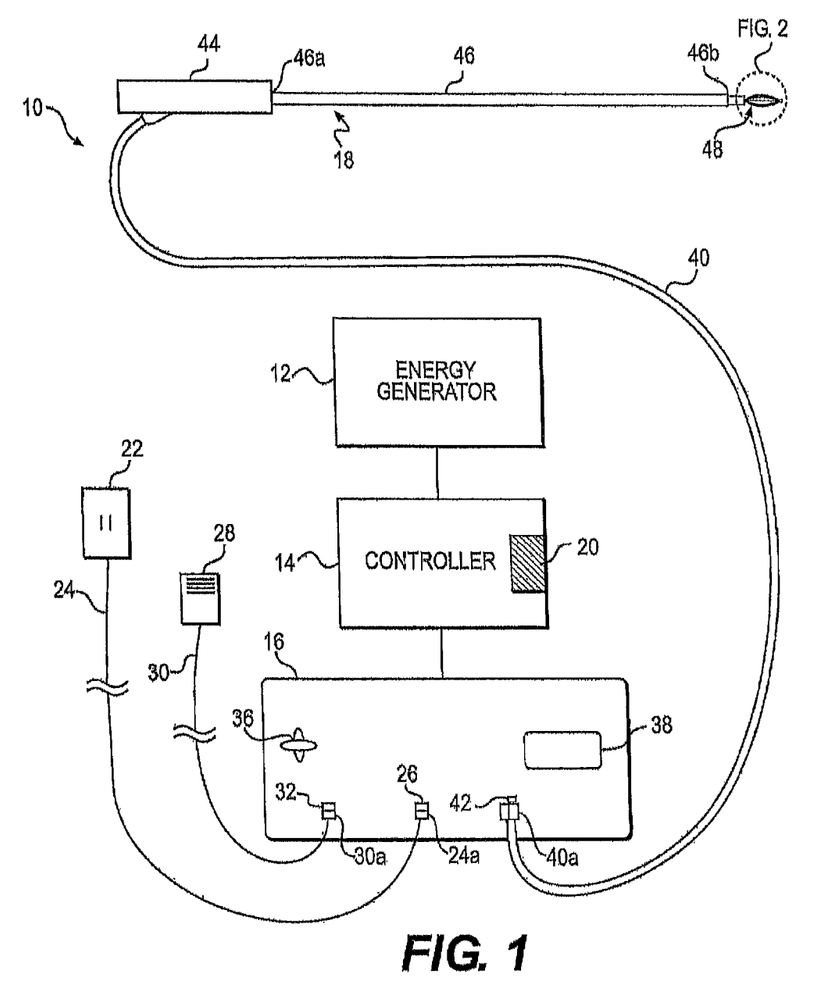
FIG. 1 illustrates a system for treating tissue in a passageway within a body, the system including an energy delivery device having an energy emitting portion, according to an embodiment of the present disclosure.

FIG. 1 illustrates an exemplary system 10. System 10 includes an energy generator 12, a controller 14, a user interface surface 16, and an energy delivery device 18. Energy generator 12 may be any suitable device configured to produce energy for heating and/or maintaining tissue in a desired temperature range. In one embodiment, for example, energy generator 12 may be an RF energy generator. The RF energy generator may be configured to emit energy at specific frequencies and for specific amounts of time in order to reverse obstruction in an airway of a lung.

In certain obstructive airway diseases, obstruction of an airway may occur as a result of narrowing due to airway smooth muscle contraction. Accordingly, in one embodiment, energy generator 12 may be configured to emit energy that reduces the ability of the smooth muscle to contract and/or increases the diameter of the airway by debulking, denaturing, and/or eliminating the smooth muscle or nerve tissue. That is, energy generator 12 may be configured to emit energy capable of killing smooth muscle cells, preventing smooth muscle cells from replicating, and/or eliminating the smooth muscle by damaging and/or destroying the smooth muscle cells.

More particularly, energy generator 12 may be configured to generate energy with a wattage output sufficient to maintain a target tissue temperature in a range of about 60 degrees Celsius to about 80 degrees Celsius. In one embodiment, for example, energy generator 12 may be configured to generate RF energy at a frequency of about 400 kHz to about 500 kHz and for treatment cycle durations of about 5 seconds to about 15 seconds per treatment cycle. Alternatively, the duration of each treatment cycle may be set to allow for delivery of energy to target tissue in a range of about 125 Joules of RF energy to about 150 Joules of RF energy. In the preferred embodiment, the duration of each treatment cycle may be set to allow for delivery of monopolar energy to target tissue for about 10 seconds at 65 degrees Celsius or, alternatively, delivery of biopolar energy in a range of about 2-3 seconds at 65 degrees Celsius.

An energy operating mechanism 22 may be associated with energy generator 12. Energy operating mechanism 22 may be any suitable automatic and/or user operated device in operative communication with energy generator 12 via a wired or wireless connection, such that energy operating mechanism 22 may be configured to enable activation of energy generator 12. Energy operating mechanism 22 may therefore include, but is not limited to, a switch, a pushbutton, or a computer. In the exemplary embodiment, energy operating mechanism 22 is a footswitch. A conductive cable 24 may extend from energy operating mechanism 22 to user interface 16, and may include a coupler 24a configured to be electrically coupled to an interface coupler 26 disposed on user interface surface 16.

Controller 14 may be coupled to energy generator 12. Controller 14 may include a processor 20 configured to receive information feedback signals, process the information feedback signals according to various algorithms, produce signals for controlling the energy generator 12, and produce signals directed to visual and/or audio indicators. For example, processor 20 may include one or more integrated circuits, microchips, microcontrollers, and microprocessors, which may be all or part of a central processing unit (CPU), a digital signal processor (DSP), an analogy processor, a field programmable gate array (FPGA), or any other circuit known to those skilled in the art that may be suitable for executing instructions or performing logic operations. That is, processor 20 may include any electric circuit that may be configured to perform a logic operation on at least one input variable. In some embodiments, processor 20 may be configured to use a control algorithm to analyze one of a reflected portion or a forward portion of the energy delivered to the targeted tissue and generate control signals for energy generator 12.

Controller 14 may additionally be coupled to and in communication with user interface 16. In the exemplary embodiment illustrated in FIG. 1, controller 14 may be electrically coupled to user interface 16 via a wire connection. In alternative embodiments, controller 14 may be in wireless communication with user interface 16. User interface 16 may be any suitable device capable of providing information to an operator of the energy delivery system 10. Accordingly, user interface 16 may be configured to be operatively coupled to each of the components of energy delivery system 10, receive information signals from the components, and output at least one visual or audio signal to a device operator in response to the information received. In the exemplary embodiment, the surface of user interface 16 includes at least one switch 36 and a digital display 38. It is contemplated that user interface may additionally include one or more audio tone indicators and/or graphical representations of components of system 10.

Energy delivery device 18 may be coupled to user interface 16. For example, a cable 40 may extend from energy delivery device 18 to user interface 16, and include a coupler 40a configured to be electrically coupled to an interface coupler 42 associated with user interface 16.

Energy delivery device 18 may include a handle portion 44, an elongate member 46, and an energy emitting portion 48. Elongate member 46 has a proximal end 46a and a distal end 46b. For purposes of this disclosure, "proximal" refers to the end closer to the device operator during use, and "distal" refers to the end further from the device operator during use. Handle portion 44 may be disposed at proximal end 46a of elongate member 46 and energy emitting portion 48 may be disposed at distal end 46b. Handle portion 44 may be any known, suitable handle having one or more actuators, switches, or the like to control movement of elongate member 46 and/or manipulate energy emitting portion 48.

Elongate member 46 extends distally from handle portion 44. Elongate member 46 may be a flexible tube, made from any suitable biocompatible material known to one of ordinary skill in the art and having sufficient flexibility to traverse tortuous anatomy. Such materials may include, but are not limited to, rubber, silicon, polymers, stainless steel, metal-polymer composites, and metal alloys of nickel, titanium, copper cobalt, vanadium, chromium, iron, and/or superelastic material such as nitinol, which is a nickel-titanium alloy.

Elongate member 46 may be a solid tube or a hollow tube. In some embodiments, elongate member 46 may include one or more lumens or channels formed therein (not shown) for the passage of a variety of surgical equipment, including, but not limited to, imaging devices and tools for irrigation, insufflation, vacuum suctioning, biopsies, and drug delivery. Elongate member 46 may further include an atraumatic exterior surface having a rounded shape and/or coating. The coating be any coating known to those skilled in the art enabling ease of movement of energy delivery device 18 through an access device such as, for example, a bronchoscope, or a passageway within the patient's body. The coating may therefore include, but is not limited to, a lubricious coating and/or an anesthetic.

Energy emitting portion 48 may be attached to and extend from distal end 46b of elongate member 46. Energy emitting portion 48 may be made out of the same piece of material as elongate member 46. Alternatively, energy emitting portion 48 may be fabricated independently by any known means and may be made permanently or removably attached to distal end 46b of elongate member 46. For example, energy emitting portion 48 may be permanently or removably attached to distal end 46b of elongate member 46 via a flexible junction enabling movement of energy emitting portion 48 relative to distal end 46b of elongate member 46.

Figure 2:
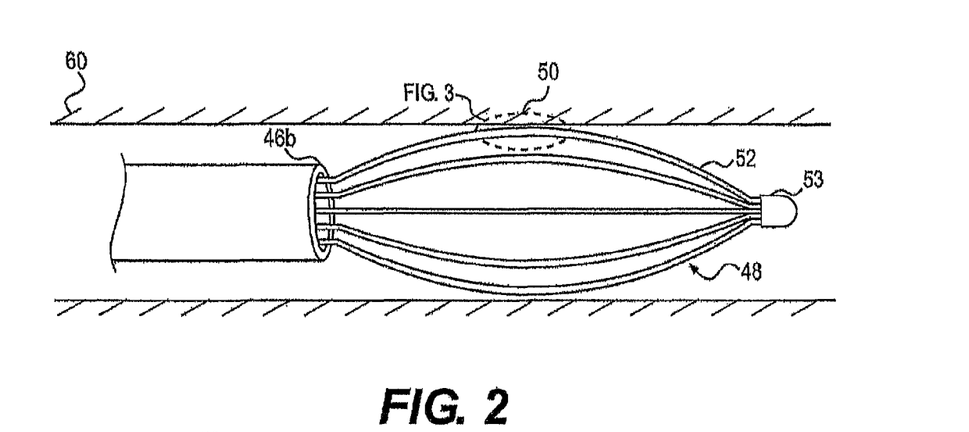
FIG. 2 is a side view of the energy emitting portion of FIG. 1, according to an embodiment of the present disclosure.

Referring to FIG. 2, energy emitting portion 48 may be any size, shape and/or configuration having dimensions that can be inserted into a passageway within a body and advanced to a treatment site 60. In the exemplary embodiment, energy emitting portion 48 may be configured to expand between a first, collapsed configuration (not shown) and a second, expanded configuration (FIG. 2) once inserted into the passageway. In the second, expanded configuration, a contact region 50 of energy emitting portion 48 may be configured to contact tissue at treatment site 60. One or more actuators (not shown) disposed on handle portion 44 may facilitate expansion of energy emitting portion 48.

Energy emitting portion 48 may have any shape, size, and/or configuration in the second, expanded configuration. In the exemplary embodiment shown in FIG. 2, energy emitting portion 48 may be a basket having a plurality of legs 52 that converge at a distal tip 53. Legs 52 may be configured so that energy emitting portion 48 forms an ovular shape in the second, expanded configuration. In this embodiment, region 50 may be the portion of basket that is the greatest distance from the longitudinal axis of energy emitting portion 48 when energy emitting portion 48 is in the second, expanded configuration. It is contemplated that legs 52 may form any other shape and/or configuration that facilitates contact between contact region 50 and tissue of treatment site 60 in the second, expanded configuration.

Legs 52 may be constructed from a material such as, for example, a shape memory metal alloy or a polymer material so that legs 28 may collapse to have a smaller cross-section in the first, collapsed configuration (not shown). Although FIG. 2, shows that that energy emitting portion 48 comprises four legs 52, energy emitting portion 48 may include any number of legs 52 (e.g., 6 legs) having any desired pattern and/or configuration. For example, legs 52 may be cylindrical, square, semi-circular, rectangular, or any other suitable shape. In addition, legs 52 may be any cross-sectional shape known in the art including, but not limited to, circular, square, or ovular.

Figure 3:
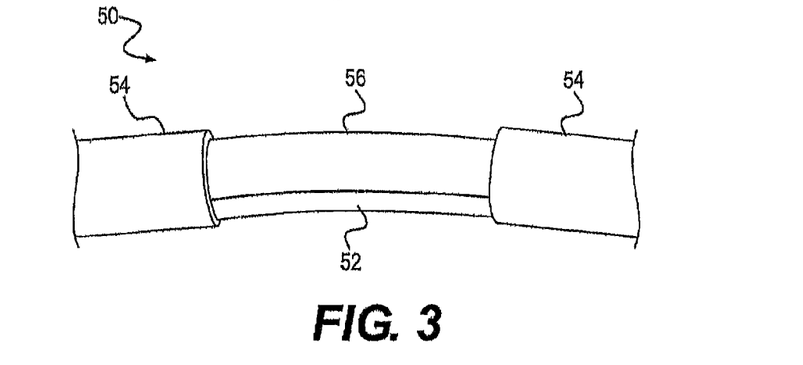
FIG. 3 is an exploded view of a portion of a leg of the energy emitting portion of FIG. 2, according to an embodiment of the disclosure.

Energy emitting portion 48 may further include at least one energy conducting element 56. The at least one energy conducting element 56 may be located along the length of at least one of the plurality of legs 52 and may include at least a portion of the contact region 50 of energy emitting portion 48. In the exemplary embodiment illustrated in FIG. 3, the at least one leg 52 of the energy emitting portion 48 is made up of a single, elongate energy conducting element 56. Portions 54 of energy conducting element 56 may have an insulating material, such as, for example, a non-conducting polymeric sheath that is heat shrunk onto each leg 52. In addition, a portion of energy conducting element 56 disposed between the insulated portions 54 may be exposed, forming an active region for delivering energy to tissue at treatment site 60.

The at least one energy conducting element 56 may be, for example, any suitable electrode known to those skilled in the art configured to emit energy. The electrode may be monopolar or bipolar. In the exemplary embodiment, energy emitting portion 48 includes monopolar electrodes. Accordingly, system 10 further includes a return electrode component configured to complete an electrical energy emission or patient circuit between energy generator 12 and a patient (not shown).

Referring back to FIG. 1, the return electrode component may include a conductive pad 28. Conductive pad 28 may include a conductive adhesive surface configured to removably stick to a patient's skin. In addition, conductive pad 28 may include a surface area having a sufficient size in order to alleviate burning or other injury to the patient's skin that may occur in the vicinity of the conductive pad 28 during energy emission. A cable 30 may extend from conductive pad 28 and may include a coupler 30a. Coupler 30a may be configured to be coupled to an interface coupler 32 on user interface surface 16 to electrically couple conductive pad 28 to the at least one energy conducting element 56.

Figure 4:
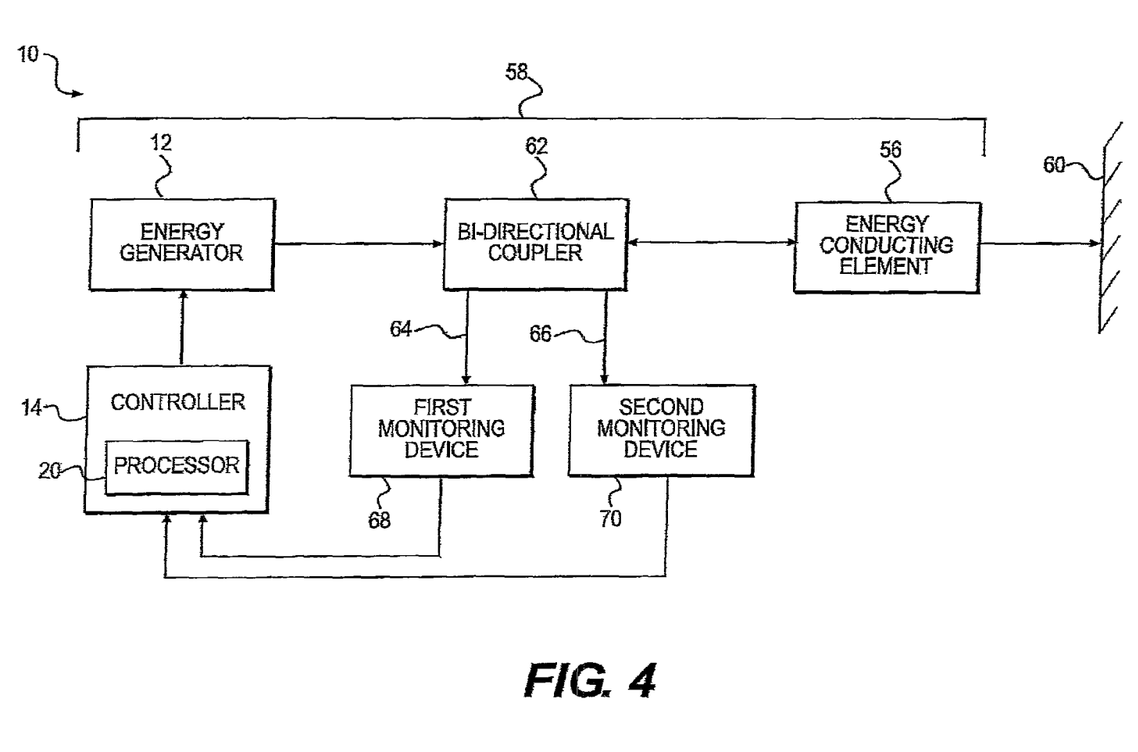
FIG. 4 is a schematic diagram of the system of FIG. 1, according to an embodiment of the disclosure.

FIG. 4 is a simplified schematic of system 10. As will be described below, components of system 10 may be configured to deliver energy to tissue at treatment site 60. In addition, components of system 10 may be configured to monitor tissue treatment.

With reference to FIG. 4, energy generator 12 of system 10 may be controlled by controller 14, and may be configured to generate a forward signal for delivering energy to tissue at treatment site 60. As discussed above, energy generator 12 may be an RF generator configured to generate a forward RF signal. The forward RF signal may be carried to the at least one energy conducting element 56 in contact with tissue at treatment site 60 via transmission line 58. Transmission line 58 broadly refers to any structure or structures designed to carry alternating current of, for example, radio frequency or microwave energy. In the exemplary embodiment, transmission line 58 may include energy generator 12, the at least one energy conducting element 56, and conducting elements therebetween including, but not limited to, cable 40, elongate member 46, and at least one of the plurality of legs 52 (not shown).

The forward RF signal carried via transmission line 58 may be supplied to the at least one energy conducting element 56. The at least one energy conducting element 56 may then deliver energy to tissue at treatment site 60. In particular, energy may be delivered through the exposed region of the at least one energy conducting element 56 in contact with tissue at treatment site 60 to raise a temperature of the tissue to a threshold temperature that ablates or otherwise alters the target tissue.

Components of system 10 may also be used to monitor tissue treatment during the treatment procedure. As will be described below, system 10 may be configured to monitor tissue treatment by using a reflected portion of the energy delivered to the at least one energy conducting element 56. The reflection of energy may be a function of the impedance of tissue at treatment site 60.

Impedance refers to an opposition to the flow of electrical current through the tissue. In certain applications, damaged (e.g., ablated) or unhealthy (e.g., cancerous tissue) tissue possesses lower characteristic impedance compared to that of healthy tissue of the same type. As tissue is treated, the characteristic impedance of the tissue may be altered. In particular the characteristic impedance will decrease.

When the impedance of transmission line 58 is tuned to match the impedance of the tissue, a substantial portion of the energy delivered via transmission line 58 may be transmitted through the at least one energy conducting element 56 to tissue at treatment site 60. When the impedance of the transmission line 58 and the impedance of the tissue at treatment site 60 are not matched, a portion of energy supplied to energy conducting element 56 may be reflected back along transmission line 58 to energy generator 12 via secondary signals. The secondary signals may have reflected power.

The magnitude of the reflected power may be proportional to the mismatch between the impedance of transmission line 58 and the impedance of tissue at treatment site 60. That is, the magnitude of the reflected power may increase as the impedance of tissue at treatment site 60 decreases during treatment. In addition, the net forward power, which is approximately equal to the difference between the forward power (associated with the forward signal) and the reflected power, may decrease.

As illustrated in FIG. 4, system 10 may include a bi-directional coupler 62 for detecting the reflected power and the forward power of the primary RF signal carried via transmission line 58. Bi-directional coupler 62 may be positioned between energy generator 12 and the at least one energy conducting element 56, and in communication with energy generator 12 and the at least one energy conducting element 56. In some embodiments, bi-directional coupler 62 may be integrally provided with energy generator 12. In other embodiments, bi-directional coupler 62 may be a separate component placed between energy generator 12 and the at least one energy conducting element 56. As shown in FIG. 4, the primary RF signal may be inputted to bi-directional coupler 62. The primary RF signal may pass therethrough unaffected and may be outputted from bi-directional coupler 62 to be transmitted to the at least one energy conducting element 56.

Bi-directional coupler 62 may be any known coupler configured to provide one or more signal sample outputs for measurement. In the exemplary embodiment, bi-directional coupler 62 may be configured to sample the forward RF signal passing therethrough and detect the forward power and the reflected power. Bi-directional coupler 62 may output a first signal 64 indicative of the forward power and a second signal 66 indicative of the reflected power to first monitoring device 68 and second monitoring device 70, respectively.

First monitoring device 68 and second monitoring device 70 may be any known electrical component configured to measure a power signal. In some embodiments, one or both of first monitoring device 68 and second monitoring device 70 may be a power meter. First monitoring device 68 and second monitoring device 70 may be in communication with processor 20 either wirelessly or via a wire connection to transmit information relating to the forward power and the reflected power. In this manner, the forward and reflected powers may be measured in real time, and changes in the net power level may be detected. Alternative known means for detecting and measuring the forward power and the reflective power are also contemplated.

Figure 5:
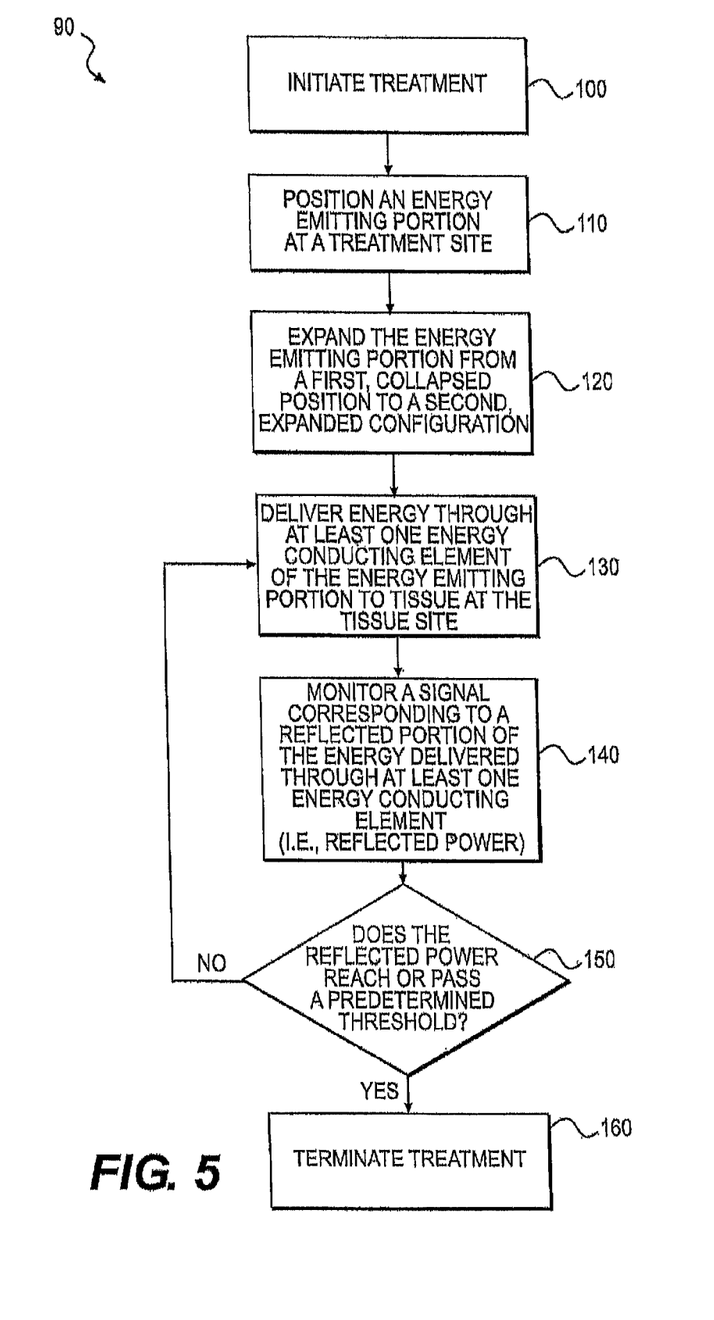
FIG. 5 is a flow diagram illustrating a method for monitoring tissue treatment by using reflected power, according to an embodiment of the disclosure.

A method for monitoring tissue treatment by using reflected power will now be described. In this exemplary embodiment, the method 90 may be used to determine the state of tissue treatment (e.g., whether the tissue has been altered and/or ablated). In some embodiments, the state of tissue treatment may be used to control the treatment procedure.

Prior to initiating the treatment procedure, controller 14 may be configured to tune transmission line 58 to have an impedance similar to the healthy tissue at treatment site 60. For example, the transmission line 58 may be tuned to have an impedance that is substantially equal to the impedance of the healthy tissue at treatment site 60, which will result in a negligible amount of reflected power. The impedance of the healthy tissue may be well-known or may be calculated by any known means.

As treatment is initiated (step 100), energy delivery device 18 may be inserted into and advanced through a passageway within a patient's body to treatment site 60. After energy emitting portion 48 has been positioned at treatment site 60 (step 110), energy emitting portion 48 may be expanded from a first, collapsed configuration to a second, expanded configuration so that contact region 50 is placed in contact with tissue at treatment site 60 (step 120).

An operator may then engage energy operating mechanism 22 to activate energy generator 12. Activation of energy generator 12 may generate a forward signal, for example, a forward RF signal, for delivery through the least one energy conducting element 56 of energy emitting portion 48 to tissue at treatment site (step 130). In particular, energy generator 12 may generate a forward signal that may be supplied to the at least one energy conducting element 56 via transmission line 58. The energy supplied to the at least one energy conducting element 56 may be delivered to tissue at treatment site 60 to raise the temperature of the tissue beyond a threshold temperature.

After the initial treatment of tissue at treatment site 60, the tissue may no longer have an impedance substantially equal to and matched with the impedance of the transmissions line 58. In particular, the impedance of the tissue at treatment site 60 may be decreased. Accordingly, a portion of the energy supplied to energy conducting element 56 may be reflected back along transmission line 58 to energy generator 12 via secondary signals. The secondary signals have reflected power. As the treatment progresses, the magnitude of the reflected power may increase.

Over the course of the treatment, bi-directional coupler 62 may be configured to sample the signal passing therethrough and output a first signal 64 indicative of forward power and a second signal 66 indicative of reflective power to first monitoring device 68 and second monitoring device 70, respectively. In some cases, first signal 64 and second signal 66 may be proportional to the forward power and the reflected power of the forward signal, respectively.

In the exemplary embodiment, second monitoring device 70 may continuously monitor the second signal 66 corresponding to the reflected power (step 140). In particular, second monitoring device 70 may monitor second signal 66 to measure the magnitude of the reflective power. Second monitoring device 70 may then transmit the measured value to processor 20.

Processor 20 may analyze the reflected power to determine the state of treatment. For example, processor 20 may be configured to execute a control algorithm or any other signal processing program to obtain a derivative of the reflected power signal. Processor 20 may then calculate from the derivative a change in slope of the reflected power signal to determine the state of treatment.

In some additional embodiments, processor 20 may be configured to compare the change in slope of the reflected power signal to a preset threshold to determine if the change in slope reaches or passes the pre-set threshold value (step 150). The preset threshold may, for example, correspond to finished treatment of tissue at treatment site 60. For example, when the change in slope of the reflected power signal is greater than the preset threshold, system 10 may continue to deliver energy to tissue. However, when the change in slope of the reflected power signal falls under the preset threshold, an operator may be notified via user interface 16 so that treatment may be terminated (step 160). In alternative embodiments, processor 20 may instead analyze the magnitude of the reflected power or voltage and compare the magnitude to a threshold. In those embodiments, operator may be notified when the magnitude of the reflected power or voltage exceeds a threshold corresponding to finished treatment.

In some alternate embodiments, the net forward power may be used to monitor treatment. As discussed above, the net forward power may decrease as the reflected power increases as a function of mismatches between the impedance of transmission line 58 and the impedance of tissue at treatment site 60. In these embodiments, the method for monitoring treatment by using the net forward power may be substantially similar to the method described above with reference to FIG. 5. In this method, however, first monitoring device 68 may continuously monitor the first signal 64 corresponding to the forward power. In particular, first monitoring device 68 may monitor first signal 64 to measure the magnitude of the forward power. First monitoring device 68 may then transmit the measured value to processor 20 for similar processing. In this embodiment, system 10 may further include one or more attenuators to facilitate measurement of the forward power.

Figure 6:
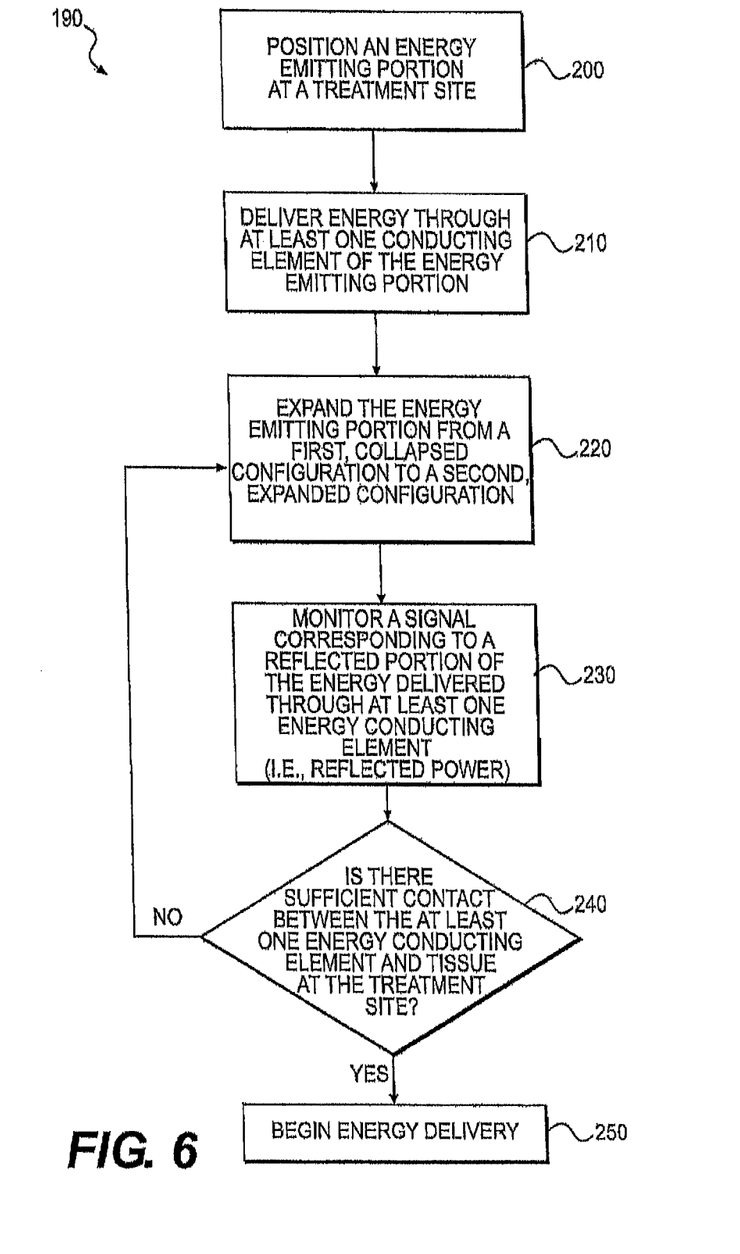
FIG. 6 is a flow diagram illustrating a method for monitoring the contact between at least one energy conducting element and tissue at a treatment site by using reflected power, according to an embodiment of the disclosure.

Another method for monitoring tissue treatment by reflected power will now be described. In this exemplary embodiment, the reflected power may be measured to determine if the at least one conducting element 56 is in contact with the tissue at treatment site 60. This method may be particularly advantageous because when the energy conducting element 56 is positioned over the tissue during operation, the operator's view of the contact between the energy conducting element 56 and the tissue may be obstructed. Thus, the method may allow the operator to determine whether sufficient contact has been established without requiring visual confirmation.

Referring to FIG. 6, the method 190 may include inserting and advancing energy delivery device 18 through a passageway within a patient's body to treatment site 60 (step 200). In this embodiment, energy delivery device 18 may have a first, collapsed configuration when energy delivery device 18 is positioned at treatment site 60.

After energy emitting portion 48 has been positioned adjacent treatment site 60 (step 200), an operator may engage energy operating mechanism 22 to activate energy generator 12, which may generate a forward signal for delivery through the least one energy conducting element 56 (step 210). In particular, energy generator 12 may generate a forward signal for delivery to the at least one energy conducting element 56 via transmission line 58. In this embodiment, a forward non-therapeutic signal of low power may be provided to prevent tissue damage. The signal may be, for example, on the order of 1-3 dBm.

Energy emitting portion 48 may be manipulated to position energy emitting portion 48 relative to tissue at treatment site 60 and/or expand energy emitting portion 44 from the first collapsed configuration to the second expanded configuration (step 220). Over the course of the positioning and expansion of energy emitting portion 48, bi-directional coupler 62 may be configured to sample the signal passing therethrough and output a first signal 64 indicative of forward power and a second signal 66 indicative of reflective power to first monitoring device 68 and second monitoring device 70, respectively. In some cases, first signal 64 and second signal 66 may be proportional to the forward power and the reflected power, respectively.

In the exemplary embodiment, second monitoring device 70 may continuously monitor the second signal 66 corresponding to the reflected power (step 230). In particular, second monitoring device 70 may monitor second signal 66 to measure the magnitude of the reflected power.

The magnitude of the reflected power may be a function of the position of the at least one conducting element 56 relative to tissue at treatment site 60. For example, the magnitude of the reflected power may differ when the at least one conducting element 56 is not in contact with tissue and when the at least one conducting element 56 is in contact with tissue. In addition, in embodiments where energy emitting portion 44 includes two or more conducting elements 56, the magnitude of the reflected power may change based on the ratio of conducting elements 56 in contact with tissue and the conducting elements 56 that are not in contact with tissue.

Processor 20 may analyze the measured reflected power to determine whether there is sufficient contact between the at least one energy conducting element 56 and tissue at the treatment site 60 (step 240). For example, processor 20 may be configured to execute a control algorithm or any other signal processing program to determine the change in slope of the reflected power signal. The change in slope may reflect an amount of contact between the at least one energy conducting element 56 and tissue at treatment site 60. For example, the smaller the slope the more likely the at least one energy conducting element 56 is in contact with tissue of treatment site 60. In some additional embodiments, processor 20 may compare the amount of contact to a threshold value to determine if there is sufficient contact between the at least one energy conducting element 56 and tissue at treatment site 60 so that the operator may begin delivering energy to tissue at treatment site 60 (step 250).

In additional and/or alternative embodiments, a method may be provided to monitor tissue impedance to detect diseased tissue at treatment site 60 prior to initiating delivery of energy to the tissue. In this embodiment, an operator may insert the exemplary energy delivery device 18 or, alternatively, a separate RF probe or other instrument into a passageway within a patient's body. The energy delivery device or RF probe may be swept across tissue at treatment site 60. The operator may monitor the reflected power. A gross change in reflected power could reflect that cancerous or other diseased tissue is present.

It is contemplated that in other embodiments, system 10 may additionally and/or alternatively directly measure impedance of tissue at treatment site 60 during treatment via one or more electrodes (not shown) in contact with the treatment site 60. An AC current may be applied to the electrodes to measure the electrode voltage. Processor 20 may analyze the measured electrode voltage and compute the impedance based on the known input signal characteristics and the measured electrode voltage. These embodiments may be found in U.S. Pat. No. 7,104,987 titled CONTROL SYSTEM AND PROCESS FOR APPLICATION OF ENERGY TO AIRWAY WALLS AND OTHER MEDIUMS, issued Sep. 12, 2006; U.S. Patent Application Publication No. 2006/0247746 A1 titled CONTROL METHODS AND DEVICES FOR ENERGY DELIVERY, published Nov. 2, 2006, and U.S. Patent Application Publication No. 2009/0030477 A1 titled SYSTEM AND METHOD FOR CONTROLLING POWER BASED ON IMPEDANCE DETECTION, SUCH AS CONTROLLING POWER TO TISSUE TREATMENT DEVICES, published Jan. 29, 2009, which are all incorporated by reference herein in their entirety.

The disclosed systems and methods may provide certain benefits. For example, the disclosed systems and methods may remove the need for thermocouples, reducing disposable costs. In addition, the systems and methods disclosed herein may result in lower costs as the components for performing the method of monitoring treatment may already be present in the system delivering energy to tissue at treatment site 60.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for treating tissue in a passageway within a body, the method comprising:
    positioning a medical device adjacent a treatment site in the passageway, the medical device including:
        a shaft having a proximal end and a distal end; and
        an energy emitting portion at or adjacent the distal end;
    supplying an amount of non-therapeutic energy from an energy source to the energy emitting portion;
    monitoring a first signal corresponding to an amount of the non-therapeutic energy being reflected back towards the proximal end of the shaft;
    when the amount of the non-therapeutic energy reflected back towards the proximal end of the shaft exceeds a contact threshold, supplying an amount of therapeutic energy from the energy source to the energy emitting portion to treat tissue at the treatment site, a first portion of the amount of therapeutic energy being transmitted through the energy emitting portion to the tissue and a second portion of the amount of therapeutic energy being reflected back towards the proximal end of the shaft; and monitoring a second signal corresponding to one of the first portion of the amount of therapeutic energy and the second portion of the amount of therapeutic energy.

2. The method of claim 1, wherein the second signal corresponds to the first portion of the amount of therapeutic energy, the second signal has a power, and wherein the power decreases during delivery of therapeutic energy to the tissue.

3. The method of claim 1, wherein the second signal corresponds to the second portion of the amount of therapeutic energy, the second signal has a power, and wherein the power increases during delivery of therapeutic energy to the tissue.

4. The method of claim 1, wherein the energy source is an RF generator.

5. The method of claim 1, further comprising:
determining a state of treatment based on the second signal.

6. The method of claim 5, wherein the monitoring of the first and second signals is performed by a bi-directional coupler.

7. The method of claim 5, wherein the second signal has a power, and wherein the method further includes determining if the power passes a power threshold.

8. The method of claim 7, wherein the method further includes terminating the supply of therapeutic energy to the energy emitting portion when the power exceeds the power threshold.

9. The method of claim 7, wherein the power threshold corresponds to a power level for ablating tissue.

10. The method of claim 5, wherein the second signal corresponds to the first portion of the amount of therapeutic energy, wherein the second signal corresponding to the reflected therapeutic energy has a power, and wherein the power is proportional to an impedance of the tissue, and the impedance of the tissue decreases during delivery of therapeutic energy to the tissue.

11. The method of claim 5, wherein the energy source is an RF generator.

12. The method of claim 5, wherein the second signal corresponds to the first portion of the amount of therapeutic energy, wherein the second signal corresponding to the reflected therapeutic energy has a power, and wherein the power is a function of an amount of tissue contact with the energy emitting portion.

13. The method of claim 5, further including analyzing the second signal to determine a rate of change in the signal, and determining an amount of contact between the tissue and the energy emitting portion based on the rate of change.

14. The method of claim 5, wherein the second signal corresponds to the first portion of the amount of therapeutic energy, and the method further includes expanding the energy emitting portion from a collapsed configuration to an expanded configuration to contact tissue, wherein the second signal corresponding to the reflected therapeutic energy has a power, and wherein the power is configured to change as the energy emitting portion contacts tissue.

15. A method for treating tissue in a passageway within a body, the method comprising:

positioning a medical device adjacent a treatment site in the passageway, the medical device including:
a shaft having a proximal end and a distal end; and
an energy emitting portion at or adjacent the distal end;
supplying an amount of non-therapeutic energy from an energy source to the energy emitting portion;
monitoring a signal corresponding to an amount of the non-therapeutic energy being reflected back towards the proximal end of the shaft; and
determining whether the energy emitting portion is in contact with tissue by comparing the amount of the non-therapeutic energy reflected back towards the proximal end of the shaft with a threshold; and
supplying an amount of therapeutic energy from the energy source to the energy emitting portion to treat the tissue only when the amount of the non-therapeutic energy reflected back towards the proximal end of the shaft exceeds the threshold and indicates contact with tissue.

16. The method of claim 15, wherein the non-therapeutic energy has a power from 1-3 dBm.

17. A method for treating tissue in a passageway within a body, the method comprising:
positioning a medical device adjacent a treatment site in the passageway, wherein the passageway is a lung passageway, the medical device including:
a shaft having a proximal end and a distal end; and
an expandable basket at or adjacent the distal end of the shaft, wherein the expandable basket is movable between a retracted configuration and one or more expanded configurations and includes a plurality of circumferentially spaced legs, wherein each of the legs includes an exposed energy emitting portion defined at first and second ends by non-conductive material;
supplying an amount of non-therapeutic RF energy from an energy source to one or more of the energy emitting portions, wherein the non-therapeutic energy has a power from 1-3 dBm;
monitoring a signal corresponding to an amount of the non-therapeutic RF energy being reflected back towards the proximal end of the shaft from the one or more of the energy emitting portions;
comparing the amount of the non-therapeutic RF energy reflected back towards the proximal end of the shaft from the one or more of the energy emitting portions to a first threshold;
when the amount of the non-therapeutic RF energy reflected back towards the proximal end of the shaft from the one or more energy emitting portions exceeds the first threshold, supplying an amount of therapeutic RF energy from the energy source to the one or more energy emitting portions to treat tissue at the treatment site, wherein the therapeutic RF energy causes the one or more energy emitting portions to reach a temperature from about 60 to 80 degrees Celsius; and
when the amount of non-therapeutic RF energy reflected back towards the proximal end of the shaft from the one or more energy emitting portions is less than the first threshold, withholding the supply of therapeutic RF energy to the one or more energy emitting portions.

18. The method of claim 17, wherein visualization of the basket is obstructed during both supplying steps.

* * * * *